United States Patent
Pranevicius et al.

(10) Patent No.: US 8,109,880 B1
(45) Date of Patent: Feb. 7, 2012

(54) NONINVASIVE METHOD TO MEASURE INTRACRANIAL AND EFFECTIVE CEREBRAL OUTFLOW PRESSURE

(76) Inventors: Osvaldas Pranevicius, New York, NY (US); Mindaugas Pranevicius, New York, NY (US); Henrikas Pranevicius, Kaunas (LT); Egidijus Marcinkevicius, Kaunas (LT); David S. Liebeskind, Los Angeles, CA (US)

( * ) Notice: Subject to any disclaimer, the term of this patent is extended or adjusted under 35 U.S.C. 154(b) by 1090 days.

(21) Appl. No.: 11/954,227

(22) Filed: Dec. 12, 2007

Related U.S. Application Data

(60) Provisional application No. 60/877,097, filed on Dec. 26, 2006.

(51) Int. Cl.
*A61B 5/02* (2006.01)
*A61B 5/00* (2006.01)

(52) U.S. Cl. ........ 600/490; 600/500; 600/504; 600/506; 600/561

(58) Field of Classification Search .................. 600/500, 600/504, 506–507, 485, 490, 561
See application file for complete search history.

(56) References Cited

U.S. PATENT DOCUMENTS

| | | | |
|---|---|---|---|
| 4,204,547 A * | 5/1980 | Allocca | 600/561 |
| 4,564,022 A | 1/1986 | Rosenfeld et al. | |
| 4,690,149 A | 9/1987 | Ko | |
| 4,819,648 A | 4/1989 | Ko | |
| 4,971,061 A | 11/1990 | Kageyama et al. | |
| 4,984,567 A | 1/1991 | Kageyama et al. | |
| 4,986,277 A * | 1/1991 | Sackner | 600/485 |
| 4,995,401 A | 2/1991 | Bunegin et al. | |
| 5,117,835 A | 6/1992 | Mick | |
| 5,411,028 A | 5/1995 | Bonnefous | |
| 5,919,144 A | 7/1999 | Bridger et al. | |
| 5,951,476 A | 9/1999 | Beach | |
| 5,951,477 A | 9/1999 | Ragauskas et al. | |
| 6,042,556 A | 3/2000 | Beach et al. | |
| 6,086,533 A | 7/2000 | Madsen et al. | |
| 6,105,582 A | 8/2000 | Pranevicius et al. | |
| 6,117,089 A | 9/2000 | Sinha | |
| 6,328,694 B1 | 12/2001 | Michaeli | |
| 6,702,743 B2 | 3/2004 | Michaeli | |

OTHER PUBLICATIONS

J Neurotrauma. 2007;24 Suppl 1:S55-8. Guidelines for the management of severe traumatic brain injury. VIII. Intracranial pressure thresholds.

Schoser B. G. et al. The impact of raised intracranial pressure on cerebral venous hemodynamics: a prospective venous transcranial Doppler ultrasonography study. "Journal of Neurosurgery" Nov. 1999:91(5): 744-9.

(Continued)

*Primary Examiner* — Miranda Le
*Assistant Examiner* — Tiffany Weston
(74) *Attorney, Agent, or Firm* — John F. Vodopia

(57) ABSTRACT

A method to measure effective cerebral outflow pressure or intracranial pressure is disclosed. The craniospinal venous system has multiple anastomoses between the jugular veins and vertebral venous plexus. Jugular veins collapse with cervical compression or head elevation, when extrinsic pressure exceeds venous pressure. The vertebral venous plexus is exposed to intracranial pressure and collapses when intracranial pressure exceeds venous pressure. Vertebral venous plexus is not compressed with head elevation or cervical compression, because enclosure in the spinal canal protects veins from the direct effects of atmospheric pressure and cervical compression. Using cervical compression and/or head elevation blood outflow is redistributed between jugular veins and vertebral venous plexus, while the degree of cervical compression or head elevation indicates effective cerebral outflow pressure or ICP.

20 Claims, 5 Drawing Sheets

OTHER PUBLICATIONS

Figure 1:
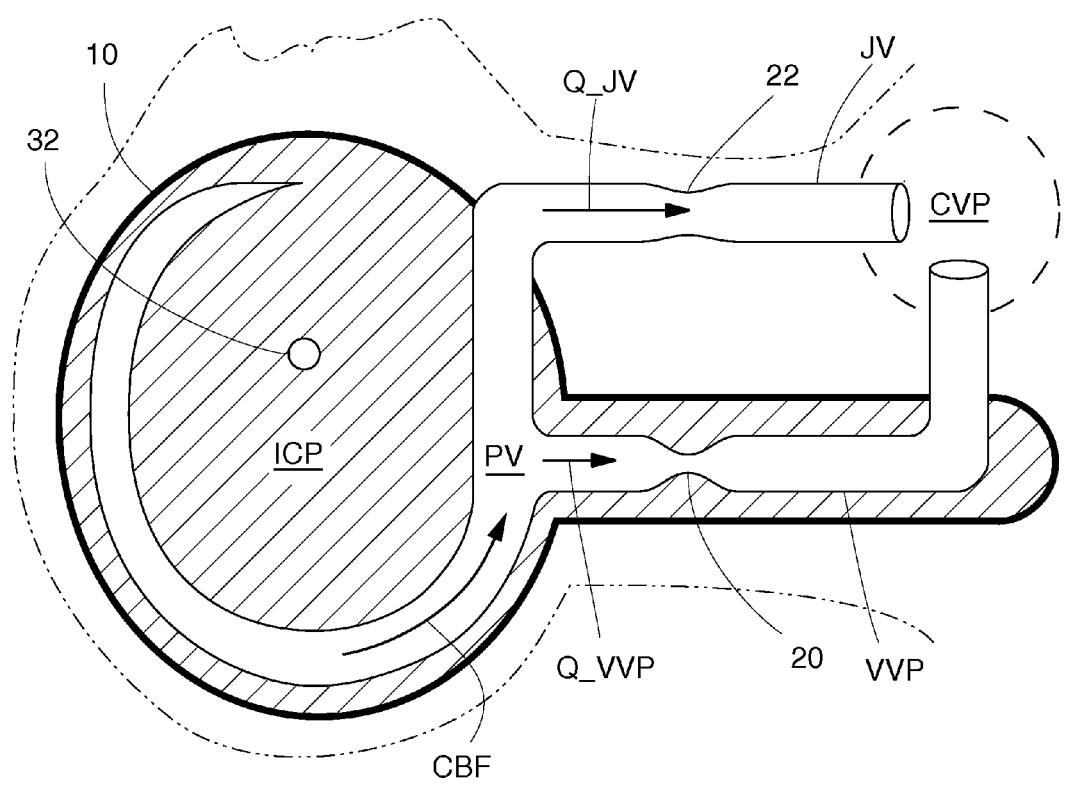

Newell D. W. Transcranial Doppler measurements. "New Horizons" Aug. 1995:3(3) 423-30. Review.

Czosnyka M. et al. Hemodynamic characterization of intracranial pressure plateau waves in head-injury patients. J Neurosurg. Jul. 1999;91(1):11-9.

Hanlo P. W. et al. Value of transcranial Doppler indices in predicting raised ICP in infantile hydrocephalus. A study with review of the literature. Childs Nerv Syst. Oct. 1995;11(10):595-603. Review.

Buki B. et al., Otoacoustic Emissions: A New Tool for Monitoring Intracranial Pressure Changes Through Stapes Displacements, Hear Res May 1996; 94 (1-2): 125-39.

Buki B. et al., Middle Ear Influence on Otoacoustic Emissions-II: Contribution of Posture and intracranial Pressure, Hear Res. Feb. 2000; 140 (1-2):202-11.

Reid A., Marchbanks R. J. et al., The Relationship Between Intracranial Pressure and Tympanic Membrane Displacement, British Journal of Audiology, 1990: 24:123-129.

Pranevicius O, Bertasius K, Pranevicius M, Jarzemskas E. Non-invasive dynamic assessment of the elasticity of intracranial structures. Acta Neurol Scand. Nov. 1992;86(5):512-6.

Pranevicius O. A noninvasive way to measure brain elastic properties and intracranial pressure dynamics. Medicina 1991 6(27):6-11. In Lithuanian.

Pranevicius M, Pranevicius O. Cerebral venous steal: blood flow diversion with increased tissue pressure. Neurosurgery. Nov. 2002;51(5):1267-73; discussion 1273-4.

Luce JM, Huseby JS, Kirk W, Butler J. Starling resistor regulates cerebral venous outflow in dogs. J Appl Physiol. Dec. 1982; 53(6):1496-1503.

Toung TJ, Miyabe M, McShane AJ, Rogers MC, Traystman RJ. Effect of PEEP and jugular venous compression on canine cerebral blood flow and oxygen consumption in the head elevated position. Anesthesiology. Jan. 1988;68 (1):53-8.

Hibino H, Matsuura M. Cerebral venous sinus pressure in seated dogs: impact of PEEP, cervical venous compression, and abdominal compression. Anesthesiology. Aug. 1985;63(2):184-9.

Toung T, Ngeow YK, Long DL, Rogers MC, Traystman RJ. Comparison of the effects of positive end-expiratory pressure and jugular venous compression on canine cerebral venous pressure. Anesthesiology. Aug. 1984;61 (2):169-72.

Grady MS, Bedford RF, Park TS. Changes in superior sagittal sinus pressure in children with head elevation, jugular venous compression, and PEEP. J Neurosurg. Aug. 1986;65(2):199-202.

Cowan F, Thoresen M. Changes in superior sagittal sinus blood velocities due to postural alterations and pressure on the head of the newborn infant. Pediatrics. Jun. 1985;75(6):1038-47.

Cowan F, Thoresen M. Ultrasound study of the cranial venous system in the human new-born infant and the adult. Acta Physiol Scand. Jan. 1983;117(1):131-7.

Chai PJ, Skaryak LA, Ungerleider RM, Greeley WJ, Kern FH, Schulman SR, Hansell DR, Auten RL, Mahaffey SF, Meliones JN. Jugular ligation does not increase intracranial pressure but does increase bihemispheric cerebral blood flow and metabolism. Crit Care Med. Nov. 1995;23(11):1864-71.

Schreiber SJ, Frank L, Rainer G, Florian D, Randolf K, Jose MV. Extrajugular pathways of human cerebral venous blood drainage assessed by duplex ultrasound. J Appl Physiol 94: 1802-1805,2003.

Pearce JM. The craniospinal venous sustem. Eur Neurol. 2006;56(2)136-8.

R. Lopez-Muniz, N.L. Stephens, B. Bromberger-Barnea, et al., Critical closure of pulmonary vessels analyzed in terms of Starling resistor models, J. Appl. Physiol. 24 (1968) 625-635.

T. Iwabuchi, E. Sobata, K. Ebina, et al., Dural sinus pressure: various aspects in human brain surgery in children and adults, Am. J. Physiol. 250 (1986) H389-H396.

* cited by examiner

NONINVASIVE METHOD TO MEASURE INTRACRANIAL AND EFFECTIVE CEREBRAL OUTFLOW PRESSURE

BACKGROUND OF THE INVENTION

1. Field of the Invention

The present invention is related to the noninvasive measurement and monitoring of the absolute value of intracranial pressure.

2. Prior Art

Intracranial pressure (ICP) is closely related to cerebral blood flow (CBF). To a first approximation, CBF is determined by the cerebral perfusion pressure (CPP). CPP is the difference between arterial blood pressure (BP) and intracranial pressure (ICP). Thus CPP=BP−ICP. Increase in ICP results in smaller values of CPP and CBF. Because of the difficulty of measuring CBF directly, BP and ICP are often measured to assess CPP. In a healthy individual, automatic regulation mechanisms in the body keep BP, ICP, and cerebral vascular resistance within a normal range and CBF is closely matched to the brain metabolic needs. These automatic regulation systems are often non-functional in brain trauma, stroke, hydrocephalic patients, and patients with liver or kidney failure, so that monitoring and management of ICP becomes a critical aspect of medical care. ICP>20 mmHg is recommended threshold for treatment in trauma patients (J Neurotrauma 2007; 24 Suppl 1:S55-8).

Current ICP monitoring techniques are generally grouped as either invasive or non-invasive.

PRIOR ART

Invasive ICP Measurement Methods

There are five common current invasive methods of measuring ICP which breach the skull: ventriculostomy, intraparenchymal catheter with built-in transducer (commonly fiberoptic), epidural transducer, subdural catheter, and subdural bolt. These have varying degrees of invasiveness. Of these methods, only a ventriculostomy can also be used to deliver therapy, which is usually draining fluid from the ventricles. The invasive methods, although medically accepted and routinely used, suffer from several drawbacks: (1) the transducer has to be calibrated before insertion; (2) the placement of the system requires a highly-trained individual; (3) there is a relatively short term (2-3 days) reliability and stability of the system, either because of leaks or plugging of the transducer, or inadvertently being disturbed, or being pulled out; (4) there are also associated risks of transducer placement such as brain damage and infection.

There are also additional drawbacks to invasive techniques. Due to the problems associated with invasive techniques for measuring ICP, standard medical protocol is to monitor ICP only for patients with scores of 8 or less on the Glasgow Coma Scale (J Neurotrauma 2007; 24 Suppl 1). It would be useful to monitor ICP of patients with Glasgow scores higher than 8. It would also be useful to monitor ICP in healthy individuals under severe environmental stress, such as astronauts, divers, and submariners.

PRIOR ART

Noninvasive ICP Measurement Methods

Many attempts have been made to use ultrasound for non-invasive intracranial pressure assessment after the pioneering work of Osvaldas Pranevicius (Medicine, 1991), where he disclosed that an ultrasound impulse transcranial travel time can detect changes in the cerebral blood volume and can be used as a method to assess intracranial pressure.

TCD has been used to provide a non-invasive, qualitative indication of variations in intra-cranial pressure ("ICP"). The use of TCD in the measurement of ICP is described, for example, in Schoser B. G. et al., "Journal of Neurosurgery" 1999, November: 91(5): 744-9; Newell D. W., "New Horizons" 1995 August:3(3) 423-30. Unfortunately, TCD only provides a qualitative indication of variations in ICP, and does not provide a quantitative measurement of ICP.

Attempts have been made to use TCD to obtain a quantitative measure of ICP using pulsatile (P.I.) and resistance (R.I.) indices. However, according to the investigations done by Czosnika M. et al. "journal of Neurosurgery", 1999, July 91(1) 11-9; and Hanlo P. W. et al. Child Neuro. Syst. 1995; October; 11(10); 595-603 there is not a linear relationship between ICP and TCD indices. Moreover, the accuracy of these TCD measurements is low, particularly in patients with raised ICP.

In Bridger in U.S. Pat. No. 5,919,144, a non-invasive system is disclosed based on real-time analysis of acoustic interaction with the brain and changes in tissue acoustic properties as ICP changes. U.S. Pat. No. 5,919,144 to Bridger et al. discloses a non-invasive apparatus and method for measuring intracranial pressure based on the properties of acoustic signals that interacted with the brain, such as acoustic transmission impedance, resonant frequency, resonance characteristics, velocity of sound, and the like. Low-intensity acoustic signals having frequencies of less than 100 kHz are used.

U.S. Pat. No. 6,086,533 to Madsen et al. discloses systems for non-invasive measurement of blood velocity based on the Doppler shift, and correlation of blood velocity before and after the manual application of an externally applied pressure, to provide a measure of intracranial pressure, ophthalmic pressure, and various other body conditions affecting blood perfusion.

U.S. Pat. No. 5,411,028 to Bonnefous discloses an ultrasonic echograph used for the measurement of various blood flow and blood vessel parameters that provide information for calculating determinations relating to the elasticity or compliance of an artery and its internal pressure.

U.S. Pat. No. 5,117,835 to Mick discloses a method and apparatus for non-invasively measuring changes in intracranial pressure by measuring changes in the natural frequency and frequency response spectrum of the skull bone. Changes in the natural frequency and frequency response spectrum of the skull are measured by applying a mechanical forced oscillation stimulus that creates a mechanical wave transmission through the bone, and then sensing the frequency response spectrum. Comparison of spectral response data over time shows trends and changes in ICP.

U.S. Pat. No. 4,984,567 to Kageyama et al. discloses an apparatus for measuring intracranial pressure using ultrasonic waves. Data from interference reflection waves caused by multiple reflections of incident ultrasonic waves at the interstitial boundaries within the cranium are analyzed for frequency, and the time difference between the element waves of the interference reflection wave is calculated and provided as output. The device described incorporates an electrocardiograph for detecting the heart beat, a pulser for generating a voltage pulse, an ultrasonic probe for receiving the pulse and transmitting an ultrasonic pulse into the cranium and receiving the echo of the incident wave, and a processor for making various calculations.

U.S. Pat. No. 5,951,476 to Beach provides a method for detecting brain microhemorrhage by projecting bursts of ultrasound into one or both of the temples of the cranium, or into the medulla oblongata, with the readout of echoes received from different depths of tissue displayed on a screen. The readouts of the echoes indicated accrued microshifts of the brain tissue relative to the cranium. The timing of the ultrasound bursts is required to be synchronized with the heart pulse of the patient.

U.S. Pat. No. 6,042,556 discloses a method for determining phase advancement of transducer elements in high-intensity focused ultrasound. Specific harmonic echoes are distributed in all directions from the treatment volume, and the temporal delay in the specific harmonic echoes provides a measure of the propagation path transit time to transmit a pulse that converges on the treatment volume.

Kageyama patented a method of amplitude measurement of ultrasound interference echoes reflected from dura mater (U.S. Pat. No. 4,971,061) in addition to a method of spectrum analysis of ultrasound interference echoes reflected from dura mater (U.S. Pat. No. 4,984,567). U.S. They describe an apparatus for measuring intracranial pressure based on the ultrasonic assay of changes in the thickness of the dura covering the brain induced by changes in ICP. However these methods are dependent upon the patients' skull condition (e.g. skull fractures, skull thickness, and pneumocephalus) as well as the patient's body temperature and environmental temperature. Each of these variables may lead to largely inaccurate ICP measurements. An additional disadvantage of these methods derives from their use of the thickness of dura mater as an indication of ICP despite the fact that dura mater, in some patients, may be adhered to the internal table of the skull.

Michaeli et al., in U.S. Pat. No. 6,702,743 and U.S. Pat. No. 6,702,743 describe determination of ICP, noninvasively, using ultrasonic backscatter representative of the pulsation of a ventricle in the head of the patient. This includes the analysis of echo pulsograms (EPG).

All the techniques, described above, involve the transmission of ultrasonic waves typically having frequencies on the order of 5 MHz into the cranium. A problem with ultrasonic excitation is the high intensities required in order to penetrate enough of the brain to sense the effect of increased ICP. Waves travelling through the intracranial region are absorbed at a substantially increasing rate as the frequency of the waves is increased. Ultrasonic frequencies on the order of 5 MHz require significant input power in order to produce usable signal-to-noise ratios. While ultrasonic input powers do not pose a health risk over relatively short time periods required for a typical clinical ultrasound scan, the FDA has limited cumulative exposure to 50 J/cm.sup.2. A 100 W/cm.sup.2 transducer utilizing one hundred 1 microsecond pulses every minute would exceed this limit in less than 100 hours. However, in some cases, patients may require continuous monitoring for at least a week.

NASA has developed a modified pulsed phase-locked loop (PPLL) method for measuring ICP based on detection of skull movements which occur with fluctuations in ICP—U.S. Pat. No. 6,117,089. Detection of skull pulsation uses an ultrasound technique in which slight changes in the distance between an ultrasound transducer and a reflecting target are measured. The instrument transmits a 500 kHz ultrasonic tone burst through the cranium, which passes through the cranial cavity, reflects off the inner surface of the opposite side of the skull, and is received by the same transducer. The instrument compares the phase of emitted and received waves and alters the frequency of the next stimulus to maintain a 90 degree phase difference between the ultrasound output and the received signal. Experimental data demonstrated that the PPLL output was highly and predictably related to directly measured ICP. This technique, however, requires highly sophisticated equipment and training, it can not be used when skull bone fractures are present—a situation very frequently encountered in the setting of traumatic brain injury.

There were several other attempts to measure intracranial pressure noninvasively.

Another method, as proposed in U.S. Pat. No. 4,564,022 to Rosenfeld et al., directs a sensory stimulus towards the patient, e.g. a flash of light into the eyes, and measures the latency of a negative-going wave of the electrical brain activity as an indicator of intracranial pressure. However latency of the visual evoked potential is not a specific indicator of ICP.

Another non-invasive ICP measurement method measures the electro-magnetic impedance response of the brain to induced fields, and correlates the response to ICP. Such electro-magnetic measurement techniques are disclosed in U.S. Pat. Nos. 4,690,149 and 4,819,648 to Ko.

Other noninvasive ICP measurement techniques that have been proposed involve determining the displacement of various tissues or body members. For example, it has been proposed, that ICP can be measured by observing the tympanic membrane of the ear. (See Buki B. et al., Otoacoustic Emissions: A New Tool For Monitoring Intracranial Pressure Changes Through Stapes Displacements, Hear Res 1996 May; 94 (1-2): 125-39; Buki B. et al., Middle Ear Influence On Otoacoustic Emissions-II: Contribution Of Posture And intracranial Pressure, Hear Res. 2000 February; 140 (1-2): 202-11; Reid A., Marchbanks R. J. et al., The Relationship Between Intracranial Pressure And Tympanic Membrane Displacement, British Journal of Audiology, 1990: 24:123-129). It has also been proposed that ICP in infants can be measured by observing the fontanelle. (See U.S. Pat. No. 4,995,401).] However, all of these proposed systems and methods suffer from at least one significant disadvantage. More specifically, while such systems and methods can be used to measure changes in ICP, such systems and methods can not be used to determine the absolute value of ICP without performing some type of calibration (for example, using known invasive techniques). This is because displacement of various internal and external tissues or body members in response to various degrees of ICP is not the same from one person to the other. For example, the degree of distension of the tympanic membrane of the ear in one patient having a certain ICP may be completely different than in another patient having the exact same ICP due to numerous factors such as age, size, thickness of the tympanic membrane, degree of dehydration, etc. Thus, without performing some type of calibration for each patient, the absolute value of ICP for that patient can not be determined using the above methods. The dilemma is that if an individual noninvasive ICP absolute value measuring device exists with acceptable accuracy for calibration of other noninvasive ICP meters, the other meters are unnecessary.

A noninvasive ICP absolute value measuring method and apparatus is presented in U.S. Pat. No. 5,951,477 to Ragauskas et al. This patent discloses the use of an ultrasonic Doppler device which detects the velocities of the blood flow inside the ophthalmic artery for both intracranial and extracranium ophthalmic artery portions, which velocities are used to calculate an absolute ICP. However, it is very cumbersome, can not be used when eye or neighboring tissue (including bones) injury is present and is imprecise to be useful in a clinical setting.

Fundoscopic examination qualitatively assesses whether ICP is elevated by observing dilatation of retinal veins. Transcranial ultrasound time of flight measurement registers variable fluctuations, however these do not register ICP directly (Pranevicius 1991, 1992).

Allocca in U.S. Pat. No. 4,204,547 describes method to measure ICP after jugular vein occlusion. Measuring pressure in the occluded venous segment it was found that pressure rise slope correlates with intracranial pressure. Alternatively noninvasive flow measurement was suggested. Pressure rise slope correlation with ICP is poor. Venous outflow model described does not take into account existence of parallel venous drainage systems-jugular veins (JV-12) and vertebral venous plexus (VVP-14).

In summary all the methods of noninvasive measurement of intracranial pressure suffer from a number of disadvantages:
  (a) They are not based on sound biophysical principles or they do not take into account the interrelationship between biophysical principles.
  (b) Most of them require expensive equipment and do not utilize existing equipment on hand.
  (c) They can not be easily performed by personnel without special training.
  (d) Most of them require calibration.
  (e) For the most part they allow measurements only in the limited setting of an intensive care unit but not in the ambulatory or even field or home settings.
  (f) Some of them have difficulty in providing reproducible measurements for the monitoring purposes.
  (g) They require head or orbital contact and as such can not be used in patients with external head and/or orbital injuries—the specific patient population who need this measurement most.
  (h) Most of them use ultrasound and as such expose brain to the high intensity acoustic energy.

BACKGROUND OF INVENTION

Objects and Advantages

The purpose of our invention is to create noninvasive intracranial pressure measurement method which also would determine whether CPP depends on ICP or CVP. In addition to that it:
  (a) would be based on sound biophysical principles;
  (b) would not require expensive equipment;
  (c) could be easily performed by personnel without special training;
  (d) would not require calibration;
  (e) would allow measurements not only in limited setting of ICU but in any situation including ambulatory and field or home setting;
  (f) would provide reproducible measurements for the monitoring purposes;
  (g) would be independent of the presence of external head and/or orbital injuries;
  (h) would minimize brain exposure to high intensity acoustic energy.

SUMMARY

In accordance with the present invention a method of measuring an intracranial pressure noninvasively comprises the steps of registering cerebral hemodynamics, then changing pressure in jugular veins to affect cerebral venous outflow, then estimating pressure in jugular veins and establishing jugular pressure value when an abrupt change in the cerebral hemodynamics occurs, whereby indicating a point when jugular venous outflow redistribution to vertebral venous plexus occurs. Jugular vein pressure value at that point is displayed as an absolute value of intracranial pressure.

DRAWINGS

Figures

Figure 2:
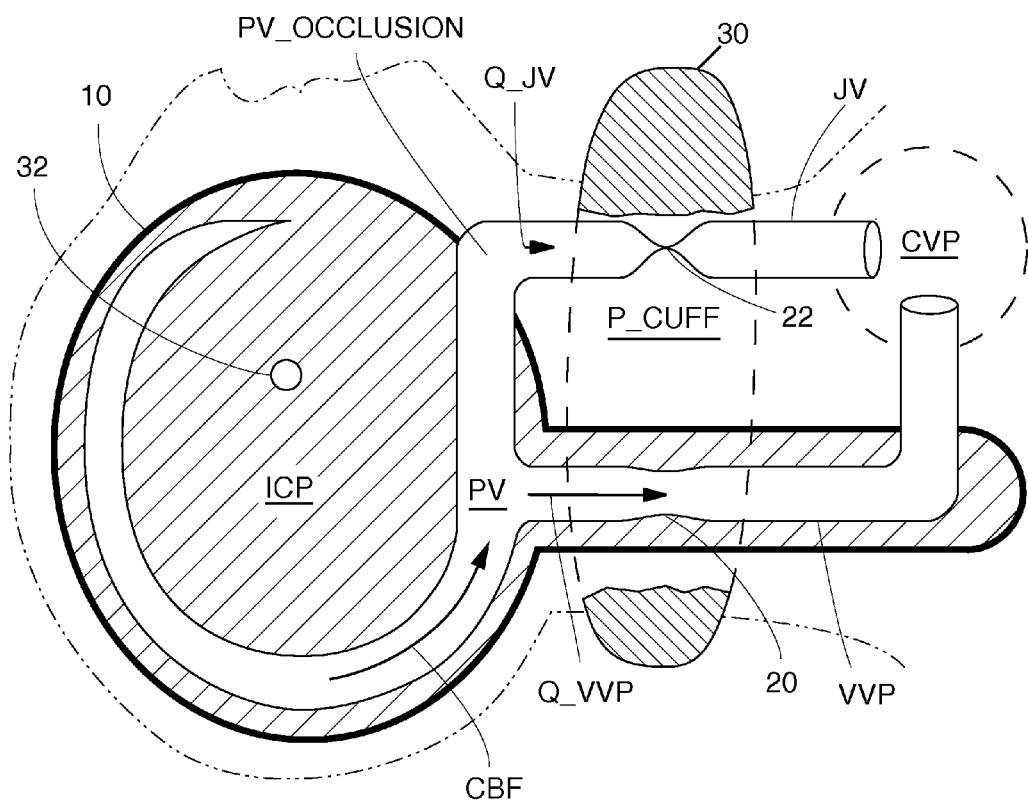
Figure 3:
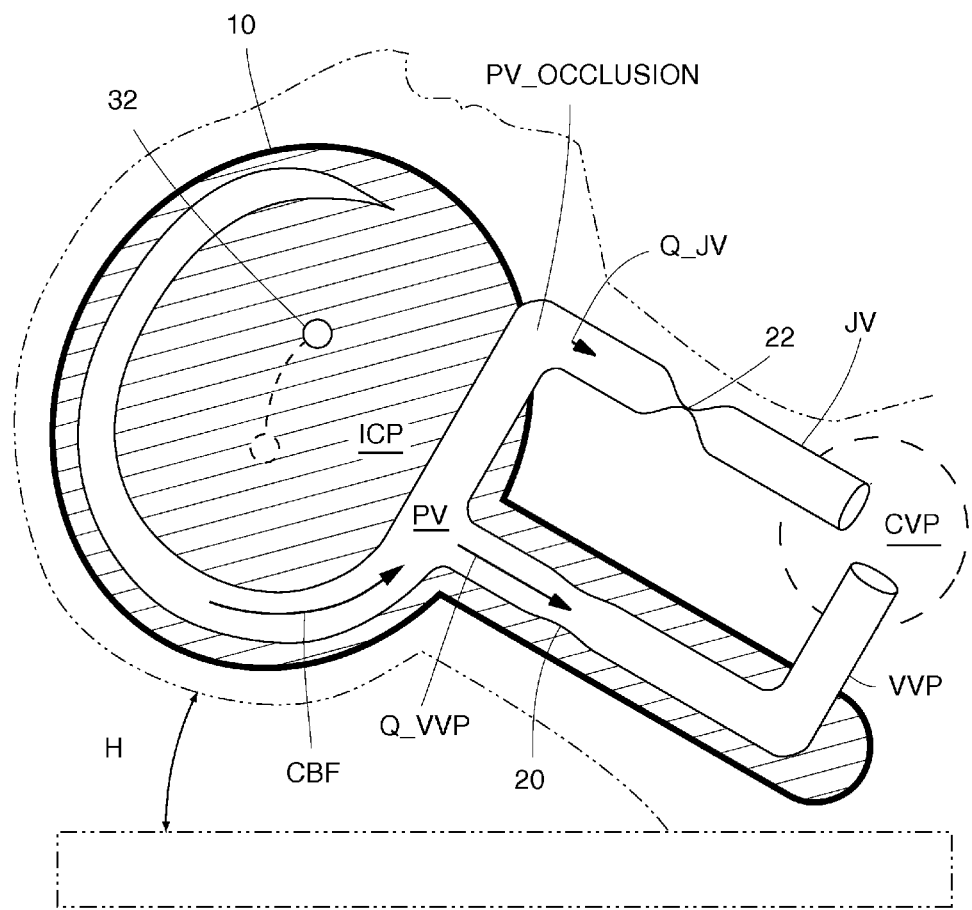
Figure 4:
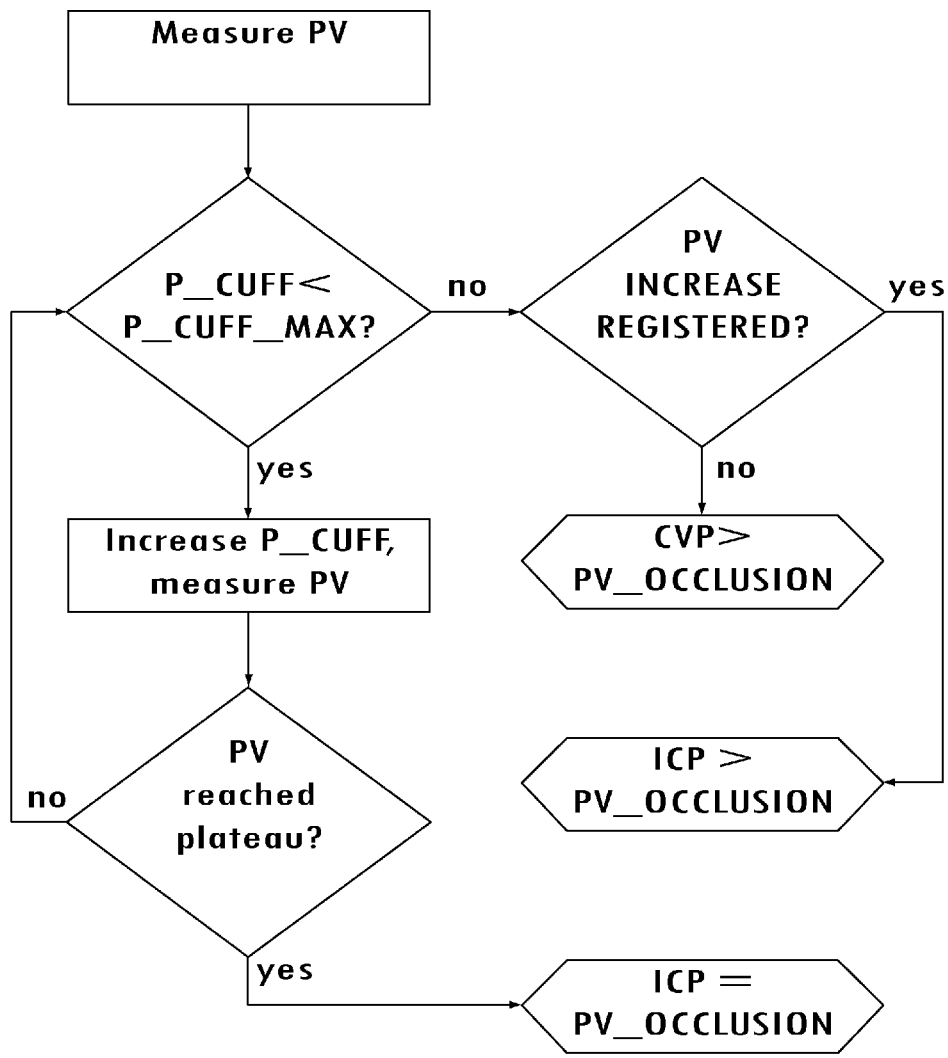
Figure 5:
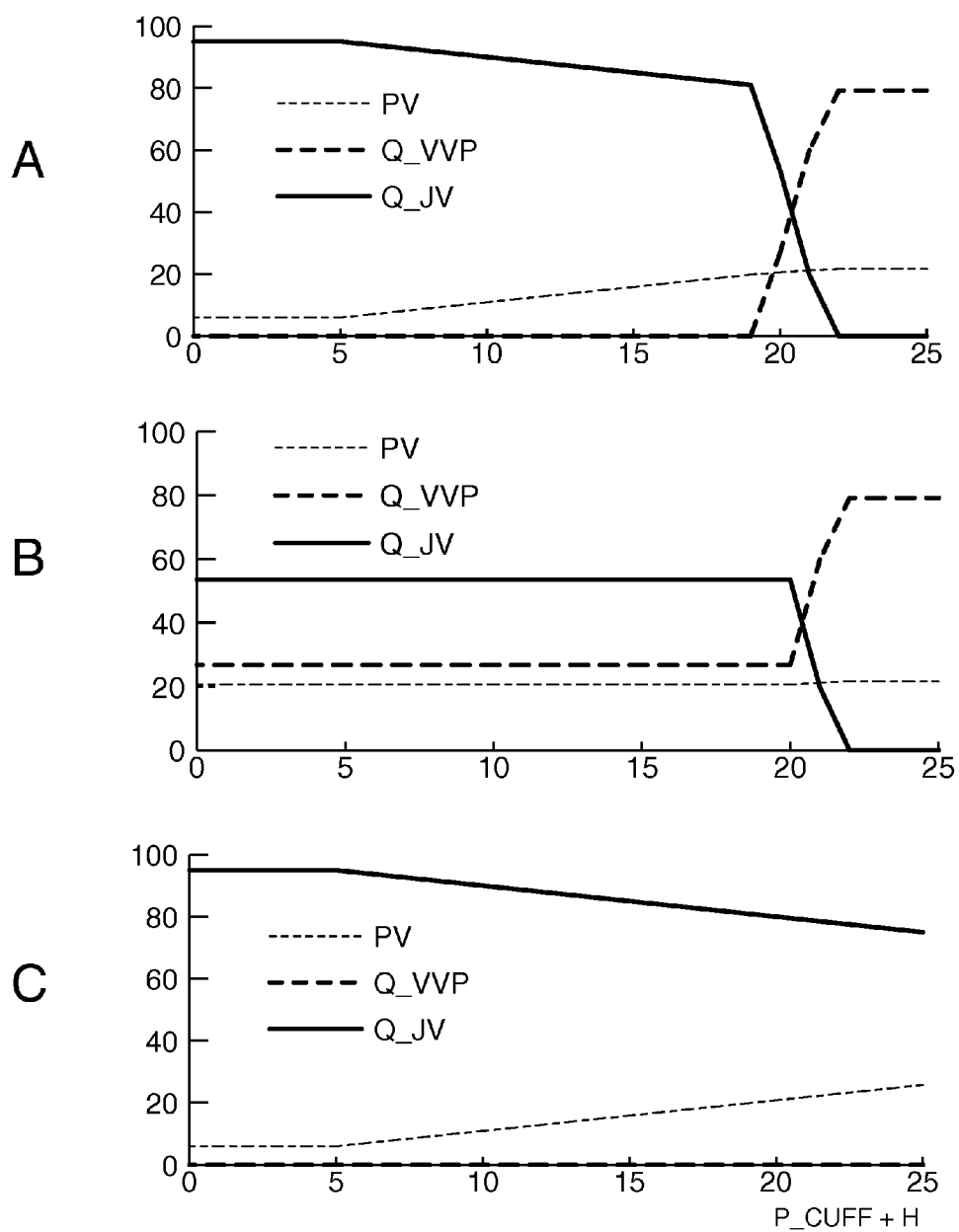

FIG. 1 shows cerebral blood outflow pathways.
FIG. 2 shows outflow diversion from jugular veins to vertebral venous plexus with cervical cuff compression.
FIG. 3 shows outflow diversion from jugular veins to vertebral venous plexus with head elevation.
FIG. 4 shows sample operation diagram.
FIGS. 5A-5C shows effect of cervical cuff occlusion on jugular venous pressure (simulation). P_CUFF_MAX=25.
FIG. 5A: CVP=5, ICP=20.
FIG. 5B: CVP=20, ICP=20.
FIG. 5C: CVP=5, ICP=30.

DRAWINGS

Reference Numerals

| Term | Definition |
| --- | --- |
| 10 | Cranium |
| PV | Cerebral venous outflow pressure |
| PV_OCCLUSION | Cerebral venous outflow pressure with jugular occlusion |
| ICP | Intracranial pressure |
| JV | Jugular veins |
| VVP | Vertebral venous plexus (intraspinal veins) |
| CVP | Central venous pressure |
| 20 | Starling resistor with area of collapse in the vertebral venous plexus |
| CBF | total cerebral outflow (cerebral blood flow) |
| 30 | Cervical compression cuff |
| 32 | external acoustic meatus |
| H | height of head elevation |
| Means to detect cerebral venous outflow (not shown) | Ultrasound, pletysmogram, manometry used to estimate pressure and flow in JV and VVP |
| Q_JV | flow via jugular veins and deep cervical veins |
| Q_VVP | low via vertebral venous plexus |
| P_CUFF | cervical cuff pressure compressing jugular veins |
| P_CUFF_MAX | maximum safe cervical cuff inflation pressure |

DETAILED DESCRIPTION

We describe the method and apparatus for noninvasive measuring of ICP and determining whether ICP or CVP determines effective cerebral outflow pressure.

The theoretical basis of our invention is the discovery of the intracranial Starling resistor (Luce, 1982) and the cerebral blood flow diversion or the cerebral venous steal model, which demonstrated outflow redistribution between the pathways with different extrinsic pressure (Pranevicius, 2002).

FIG. 1 Cerebral Blood Outflow Pathways

Blood from the cranium 10 and spinal canal flows via jugular veins Pi and vertebral venous plexus VVP. These outflow pathways have multiple anastomoses and form craniospinal venous system (Pearce J M, 2006).

Thus total venous outflow from the cranium (CBF) divides into outflow via internal jugular veins (Q_JV) and vertebral venous plexus (Q_VVP). We have termed venous drainage via the spinal canal, Q_VVP, and all extraspinal drainage as jugular outflow (Q_JV). In this functional definition Q_JV comprises flow via jugular veins, deep cervical veins and extraspinal venous plexus. The functional difference between jugular and intraspinal pathways is that extrinsic neck pressure obstructs jugular but not the vertebral outflow.

Starling Resistor

Starling resistor is used to describe flow in collapsible tubes with extrinsic compression. Flow via collapsible tube ceases when extrinsic pressure exceeds inflow pressure (like West zone 1 in lung circulation). When extrinsic pressure is smaller than inflow pressure but higher than the outflow pressure, flow is determined by difference between inflow and extrinsic pressure, while outflow pressure does not affect the flow (zone 2). When extrinsic pressure is smaller than the outflow pressure, it has no effect on flow, which is then determined by difference between inflow and outflow pressure (zone 3). Pranevicius & Pranevicius described flow redistribution between two parallel starling resistors (Neurosurgery, 2002).

Starling resistor is found to exist in the intracranial veins and pressure in the collapsible intracranial veins was found to be equal to ICP (Luce, 1982). A collapsible segment of the intracranial and intraspinal veins is shown schematically in FIG. 1 20. For this resistor inflow pressure is cerebral venous pressure PV, extrinsic pressure is ICP and outflow pressure is CVP.

Internal jugular veins also act as a Starling resistor 22 and their collapse was described whenever venous pressure becomes negative in regard to atmospheric pressure with head-up tilt. (Gisolf, 2004). For jugular veins inflow pressure is PV, outflow—CVP and extrinsic—atmospheric or cervical compression pressure.

In the supine position most of the venous outflow from the cranium occurs via jugular veins JV (Q_JV>Q_VVP, (FIG. 1). During head up tilt flow redistributes to VVP and jugular veins JV partially collapse (Gisolf, 2004), FIG. 3. In preferred embodiment Flow redistribution is induced with cervical cuff 30 which exerts extrinsic pressure P_CUFF and causes jugular vein to collapse (22) (FIG. 2).

We use venous steal model with two parallel Starling resistors (Pranevicius, 2002) to describe cerebral blood outflow. Flow diversion was also demonstrated in an experiment-Q_VVP increased with neck compression in volunteers (Schreiber, 2003).

Blood leaves the cranium 10 through the interconnected craniospinal venous system (JV and VVP) which has mean pressure PV. They empty into vena cava which has central venous pressure CVP. Collapsible intracranial veins and veins of vertebral venous plexus WP are exposed to ICP (20) and were shown to behave as starling resistor. Proximal venous pressure PV is approximates ICP or central venous pressure (CVP), whichever is higher (CVP<=PV>=ICP). Total venous outflow CBF is distributed between jugular veins IV (Q_JV) and VVP (Q_VVP).

$$CBF = Q\_JV + Q\_VVP \quad (1)$$

Flow calculations via two parallel Starling resistors were done using venous steal model (Pranevicius, 2002) and are represented in FIGS. 5A-5C.

Pressure in the craniospinal venous system PV approximates ICP. To find it we must determine minimal pressure in the jugular veins at witch most cerebral venous outflow (CBF) will be diverted to WP. Then $$Q\_VVP >> Q\_JV$$

$$PV \approx ICP.$$

FIGS. 2 and 5A-5C

Preferred Embodiment

Jugular veins iv are occluded (22) with an inflatable cervical cuff 30 and equilibrium pressure PV is measured in the head or cervical vein. This occlusion pressure PV represents effective outflow pressure (ICP if ICP is higher than CVP).

To measure PV with iv occlusion, pressure in the head or cervical vein is measured and cervical cuff 30 is gradually inflated. Vein pressure PV plateau when further cuff inflation does not increase venous pressure is displayed as PV_OCCLUSION. Cuff inflation is limited to a maximum safe cuff pressure P_CUFF_MAX, which is selected below diastolic arterial pressure and inspiratory airway occlusion pressure. P_CUFF_MAX may be selected as 20 mmHg (ICP treatment threshold) or higher. If initial PV is high and does not increase with extrinsic compression, effective cerebral outflow pressure is said to be determined by CVP, not the ICP. If PV increases with P_CUFF inflation but does not reach the plateau at P_CUFF_MAX, the effective outflow pressure or ICP is displayed as higher than P_CUFF_MAX.

Apparatus comprises means to compress neck veins 30 (like inflatable or liquid filled cervical tourniquet with pressure P_CUFF) and means to register blood flow/pressure and/or volume in the jugular veins and extrajugular vertebral venous plexus (like Doppler ultrasound or B-mode with color Doppler, or pletysmogram or, manometry-not shown).

In alternative embodiment cuff inflation pressure is used to estimate effective outflow pressure. Cervical cuff is gradually inflated not to exceed P_CUFF_MAX. Effect on the jugular outflow is assessed with doppler, pletysmogram or similar measure. Cuff pressure P_CUFF is said to estimate effective outflow pressure if further increase of P_CUFF does not provide higher degree of occlusion estimated by flow or volume measures, while decreasing P_CUFF results in increased flow Q_JV or decreased volume. This value of P_CUFF is an estimate of effective outflow pressure or ICP.

FIGS. 3 and 5A-5C

Alternative Embodiment

In another embodiment outflow redistribution is achieved with head-up tilt. In this embodiment extrinsic cervical pressure stays the same (atmospheric), while intraluminal pressure is lowered with head-up tilt by hydrostatic column of the height H (reference external acoustic meatus 32 to the right atrium-labeled CVP). Jugular flow Q_JV or volume is estimated with H=0. Further head elevation causes jugular compression 22 and outflow redistribution to VVP. Head elevation height H at which significant portion of jugular flow is diverted to WP (20-80%, or Q_VVP≈Q_JV) corresponds to effective outflow pressure or ICP.

Alternative Embodiments

These include alternative means to increase venous pressure PV, alternative means to register effect of venous pressure increase. In yet another embodiment cerebral blood flow CBF is estimated with transcranial Doppler ultrasound measuring middle cerebral artery (MCA) blood flow linear velocity. Jugular outflow Q_JV is calculated as mean jugular linear flow times the jugular crossection area. Relative reduction of the jugular flow with cervical compression or head-up tilt reflects outflow diversion towards VVP. The height of head elevation or the degree of neck compression at the point when cerebral outflow is diverted towards VVP corresponds to the effective outflow pressure or ICP.

In yet another embodiment Q_VVP and Q_JV is assessed directly with ultrasound and their ratio is determined at different degrees of cervical compression or head elevation. Like in the previous embodiment degree of cervical compression at which cerebral outflow is nearly equally distributed between VVP and jugular veins JV corresponds to effective outflow pressure or ICP.

In yet another embodiment head is elevated or neck is compressed to simulate predetermined effective cerebral outflow pressure value (corresponding to treatment or diagnostic threshold-lets say 20 mm Hg). If this does not result in significant cerebral outflow diverson, ICP is then estimated to be above said threshold value.

(1) Venous pressure can be changed with tonometric compression device, such as cuff or tonometric sensor over jugular vein with complete or partial contralateral vein occlusion.
(2) Venous pressure can be changed with an inflatable cervical cuff 30.
(3) Venous pressure can be changed with Valsalva maneuver/PEEP.
(4) Venous pressure can be changed by changing body position, such as reverse Trendelenburg position or head tilt.
(5) Venous pressure can be directly measured with an intravascular catheter.
(6) Effect on venous flow can be assessed via Doppler, B-mode scan, color Doppler.
(7) Effect on blood volume can be assessed with plethysmogram or time of flight measurement.
(8) Venous flow can be assessed along the spinal canal, as well.

LITERATURE (1) Luce J M, Huseby J S, Kirk W, Butler J. Starling resistor regulates cerebral venous outflow in dogs. J Appl Physiol. 1982 December; 53(6):1496-1503.
(2) Pranevicius O. A noninvasive way to measure brain elastic properties and intracranial pressure dynamics (Lithuanian). Medicina. 1991 June 6 (27): 6-11.
(3) Pranevicius O., Bertasius K., Pranevicius M., Jarzemskas E. "Noninvasive dynamic assessment of the elasticity of intracranial structures", Acta Neurol Scand 86:512-516; 1992.
(4) Pranevicius M, Pranevicius O. Cerebral venous steal: blood flow diversion with increased tissue pressure. Neurosurgery. 2002 November; 51(5):1267-73; discussion 1273-4.
(5) Toung T J, Miyabe M, McShane A J, Rogers M C, Traystman R. J. Effect of PEEP and jugular venous compression on canine cerebral blood flow and oxygen consumption in the head elevated position. Anesthesiology. 1988 Janruary; 68(1):53-8.
(6) Hibino H, Matsuura M. Cerebral venous sinus pressure in seated dogs: impact of PEEP, cervical venous compression, and abdominal compression. Anesthesiology. 1985 August; 63(2):184-9.
(7) Toung T, Ngeow Y K, Long D L, Rogers M C, Traystman R J. Comparison of the effects of positive end-expiratory pressure and jugular venous compression on canine cerebral venous pressure. Anesthesiology. 1984 August; 61(2): 169-72.
(8) Grady M S, Bedford R F, Park T S. Changes in superior sagittal sinus pressure in children with head elevation, jugular venous compression, and PEEP. J Neurosurg. 1986 August; 65(2):199-202.
(9) Cowan F, Thoresen M. Changes in superior sagittal sinus blood velocities due to postural alterations and pressure on the head of the newborn infant. Pediatrics. 1985 Junruary; 75(6):1038-47.
(10) Cowan F, Thoresen M. Ultrasound study of the cranial venous system in the human new-born infant and the adult. Acta Physiol Scand. 1983 Janruary; 117(1):131-7.
(11) Chai P J, Skaryak L A, Ungerleider R M, Greeley W J, Kern F H, Schulman S R, Hansell D R, Auten R L, Mahaffey S F, Meliones J N. Jugular ligation does not increase intracranial pressure but does increase bihemispheric cerebral blood flow and metabolism. Crit Care Med. 1995 November; 23(11):1864-71.
(12) Schreiber S J, Frank L, Rainer G, Florian D, Randolf K, Jose M V. Extrajugular pathways of human cerebral venous blood drainage assessed by duplex ultrasound. J Appl Physiol 94: 1802-1805, 2003.
(13) Guidelines for the management of severe traumatic brain injury, 3rd edition. J Neurotrauma 2007; 24 Suppl 1.
(14) Pearce J M. The craniospinal venous sustem. Eur Neurol. 2006; 56(2) 136-8.

What is claimed is:

1. A method of measuring an intracranial pressure of a subject non-invasively comprising the steps of:
   (a) placing an inflatable cervical cuff around the neck of the subject;
   (b) gradually tilting the upper body of the subject, whereby the subject's transmural jugular venous pressure is changed hydrostatically;
   (c) measuring the subject's hydrostatic pressure gradient between supine and tilted position;
   (d) selecting the subject's maximal safe cervical cuff inflation pressure level; then
   (e) gradually inflating the cervical cuff no higher than the maximal safe cervical cuff inflation pressure level, whereby the subject's transmural jugular venous pressure is changed by external compression;
   (f) testing the subject's jugular hemodynamic change in response to the transmural jugular pressure change;
   (g) if said subject's jugular hemodynamic change cannot be registered, displaying first message, that effective cerebral outflow pressure is determined by central venous pressure, whereby indicating that intracranial pressure in not intrinsically elevated and cerebral outflow is determined solely by the central venous pressure;
   (h) if said subject's jugular hemodynamic change is registered, gradually increasing cervical cuff pressure level until said subject's jugular hemodynamic change reaches plateau;
   (i) adding said hydrostatic pressure gradient to the minimal cervical cuff pressure inflation pressure level at which said subject's jugular hemodynamic change reaches plateau;
   (j) displaying the result of said addition calculated in step (i) as the subject's intracranial pressure, whereby no further jugular vein hemodynamic change can be registered with further cervical cuff inflation or hydrostatic jugular venous pressure decrease, because cerebral venous outflow was redirected into the vertebral venous system and intracranial pressure is the effective cerebral outflow pressure;
   (k) if said subject's jugular hemodynamic change is registered, but does not reach plateau, displaying the message

11 that intracranial pressure is higher than the result of said addition calculated in step (i).

2. A method of measuring intracranial pressure of the subject non-invasively as recited in claim 1, wherein said step (d) of selecting the subject's safe maximal cervical cuff inflation level comprises the steps of:
establishing arterial diastolic pressure level;
establishing inspiratory airway occlusion pressure level;
selecting lower pressure level between the arterial diastolic pressure level and the inspiratory airway occlusion pressure level; and
establishing lower pressure level between the arterial diastolic pressure level and the inspiratory airway occlusion pressure level as a safe maximal cervical cuff inflation pressure level.

3. A method of measuring intracranial pressure of the subject non-invasively as recited in claim 1, wherein said step (d) of testing the subject's safe maximal cervical cuff inflation level is performed by selecting the inflation level at 20 mm Hg.

4. A method of measuring intracranial pressure of the subject non-invasively as recited in claim 1, wherein the said step (f) of testing the subject's jugular hemodynamic change is performed by measuring volumetric flow in the subject's jugular vein.

5. A method of measuring intracranial pressure of the subject non-invasively as recited in claim 1, wherein said step (f) of testing the subject's jugular hemodynamic change is determined by measuring blood flow velocity in the subject's jugular vein.

6. A method of measuring intracranial pressure of the subject non-invasively as recited in claim 5, wherein said step (f) of testing the subject's jugular hemodynamic change is performed by measuring Doppler shift in the subject's jugular vein.

7. A method of measuring intracranial pressure of the subject non-invasively as recited in claim 1, wherein said step (f) of testing the subject's jugular hemodynamic change is performed by estimating blood volume in the subject's jugular vein.

8. A method of measuring intracranial pressure of the subject non-invasively as recited in claim 7, wherein said step (f) of testing the subject's jugular hemodynamic change comprises performing plethysmography in proximity of the subject's jugular vein.

9. A method of measuring intracranial pressure of the subject non-invasively as recited in claim 1, wherein said step (f) of testing the subject's jugular hemodynamic change is performed by measuring pressure in the subject's jugular vein.

10. A method of measuring intracranial pressure of the subject non-invasively as recited in claim 1, wherein said step (f) of testing the subject's jugular hemodynamic change is performed by measuring pressure in any of the subject's extra-cranial veins.

11. A method of measuring an intracranial pressure of a subject non-invasively comprising the steps of:
(a) estimating the subject's cerebral venous outflow redistribution between jugular venous outflow and extra-jugular venous outflow;
(b) decreasing the subject's transmural jugular vein pressure, whereby cerebral venous outflow redistribution shifts from predominantly jugular to predominantly extra-jugular venous outflow;
(c) estimating the subject's transmural jugular vein pressure; and
(d) displaying said transmural jugular venous pressure value as an absolute value of intracranial pressure, whereby no further shift in the cerebral venous outflow redistribution occurs and intracranial pressure is the effective cerebral outflow pressure.

12. A method of measuring intracranial pressure of the subject non-invasively as recited in claim 11, wherein said step (a) of estimating the subject's cerebral venous outflow redistribution comprises performing magnetic resonance imaging of the subject's cerebral blood flow.

13. A method of measuring intracranial pressure of the subject non-invasively as recited in claim 11, wherein said step (a) of estimating the subject's cerebral venous outflow redistribution comprises the steps of:
measuring blood flow in the subject's jugular vein;
measuring blood flow in the subject's vertebral venous plexus; and
estimating different between blood flow in the subject's jugular vein and in the subject's vertebral venous plexus.

14. A method of measuring intracranial pressure of the subject non-invasively as recited in claim 11, wherein said step (a) of estimating the subject's cerebral venous outflow redistribution is performed by monitoring pulsatility index in a major intracerebral artery of the subject.

15. A method of measuring intracranial pressure of the subject non-invasively as recited in claim 11, wherein said step (a) of estimating the subject's cerebral venous outflow redistribution is performed by measuring volume of the subject's jugular vein.

16. A method of measuring intracranial pressure of the subject non-invasively as recited in claim 11, wherein said step (a) of estimating the subject's cerebral venous outflow redistribution is performed by measuring blood flow velocity in the subject's jugular vein.

17. A method of measuring intracranial pressure of the subject non-invasively as recited in claim 11, wherein said step (1) of estimating the subject's cerebral venous outflow redistribution is performed by measuring pressure in the subject's jugular vein.

18. A method of measuring intracranial pressure of the subject non-invasively as recited in claim 11, wherein said step (b) decreasing the subject's transmural jugular vein pressure comprises changing the head tilt of the subject, whereby hydrostatic pressure between the subject's jugular vein and the subject's right atrium is changed.

19. A method of measuring intracranial pressure of the subject non-invasively as recited in claim 11, wherein said step (b) decreasing the subject's transmural jugular vein pressure is performed by applying an external pressure in the area of the subject's jugular vein.

20. A method of measuring intracranial pressure of the subject non-invasively as recited in claim 11, wherein said step (b) decreasing the subject's transmural jugular vein pressure comprises combination of performing a head-up tilt of the subject and applying an external pressure in the area of the subject's jugular vein.

\* \* \* \* \*